United States Patent [19]
Wilderbeek et al.

[11] Patent Number: 5,897,852
[45] Date of Patent: Apr. 27, 1999

[54] CONTAINER WITH FREEZE-DRIED VACCINE COMPONENTS

[75] Inventors: Antonius Theodorus Maria Wilderbeek, Well; Hans Almer Middelbeek, Oss, both of Netherlands

[73] Assignee: Akzo Nobel, N.V., Arnhem, Netherlands

[21] Appl. No.: 08/803,660

[22] Filed: Feb. 21, 1997

[30] Foreign Application Priority Data

Mar. 7, 1996 [EP] European Pat. Off. ............. 96200621

[51] Int. Cl.⁶ ............................ A61K 49/00; G01N 33/15
[52] U.S. Cl. .................. 424/10.3; 424/184.1; 424/204.1
[58] Field of Search .................................. 424/1.11, 1.17, 424/9.1, 10.3, 193.1, 196.11, 197.11, 201.1, 202.1, 203.1, 204.1; 206/223, 569, 570, 367

[56] References Cited

U.S. PATENT DOCUMENTS

| | | | |
|---|---|---|---|
| 3,655,838 | 4/1972 | Price et al. | 264/13 |
| 3,857,423 | 12/1974 | Ronca, Jr. | 141/5 |
| 3,893,280 | 7/1975 | King | 53/37 |
| 3,932,943 | 1/1976 | Briggs et al. | 34/5 |
| 4,295,280 | 10/1981 | Krupey | 34/5 |
| 4,351,158 | 9/1982 | Hurnitz et al. | 62/60 |
| 4,712,310 | 12/1987 | Roy | 34/5 |
| 4,981,685 | 1/1991 | Healey | 424/92 |
| 5,270,057 | 12/1993 | de Meere et al. | 424/499 |
| 5,324,511 | 6/1994 | Rotering et al. | 424/87 |

FOREIGN PATENT DOCUMENTS

| | | |
|---|---|---|
| A 475409 | 3/1992 | European Pat. Off. . |
| A1395651 | 5/1975 | United Kingdom . |
| WOA 9013285 | 11/1990 | WIPO . |
| WOA 9425005 | 11/1994 | WIPO . |

*Primary Examiner*—José G. Dees
*Assistant Examiner*—Dameron Jones
*Attorney, Agent, or Firm*—Mary E. Gormley

[57] ABSTRACT

The present invention relates to a vaccine container that contains one or more freeze-dried vaccine components. The vaccine component or components are present in two or more freeze-dried bodies, at least one of which is a lyosphere.

Furthermore, the invention relates to methods for the preparation of such a vaccine container.

Also, the invention relates to a vaccine pack, comprising the vaccine container.

12 Claims, No Drawings

CONTAINER WITH FREEZE-DRIED VACCINE COMPONENTS

The present invention relates to a vaccine container with one or more freeze-dried vaccine components, and to methods for the preparation of such a container.

It is well-known, that biological materials in solutions are susceptible to such varying influences as heat, oxidising reagents, salts etc. etc.

Several methods have been developed in order to reduce these detrimental effects in general and especially during storage.

Storage below zero degrees Celcius in a refrigerator is e.g. well-known method. Also often used is storage at −70° C. At even lower temperatures, e.g. in liquid nitrogen, many biological materials, e.g. living cells can successfully be stored even for many years.

Another well-known way of conservation is freeze-drying. During freeze-drying the solution containing the biological material is first frozen and next the water is evaporated under high vacuum and (usually) subzero temperature.

Freeze-dried biological materials can be stored and kept in an unchanged condition for many years.

An important advantage is that storage temperatures for freeze-dried biological materials may well be above zero degrees, without being detrimental to the materials.

Freeze-drying of biological material can be done according to all well-known standard freeze-drying procedures.

For diagnostic tests, it is possible to combine the buffers and enzymes in one single container and to freeze-dry the contents of this container. This approach however fails in most cases, since the various reagents should not be allowed to react with each other before the material to be tested is added. This problem was originally solved by Price (U.S. Pat. No. 3,655,838) who described a method for separate freeze-drying of the various solutions comprising the various biological materials for the diagnostic test. This method shortly exists in bringing droplets of each solution in direct contact with liquid nitrogen. This leads to instantaneous freezing. The frozen droplets can be easily transferred to a freeze-dryer and subsequently be dried. The resulting dry spheres are called lyospheres. The first lyospheres owed their form and name to the fact that they were frozen as spherical droplets and subjected to lyophilisation afterwards. It is obvious that small amounts of fluid in any possible form can also be frozen by contacting them with cold surfaces, e.g. by adding some fluid to small holes in a cold heat-conducting surface, followed by lyophilisation.

These variations on an old theme are all termed lyospheres.

The above mentioned method by Price allows to bring together in one container various components, each in their own freeze-dried lyosphere, thus avoiding premature reaction. The method is however rather labour-intensive: it requires e.g. the separate production of each different type of lyosphere, and the additional step of adding several lyospheres to one single container.

Therefore, more efficient alternatives for the invention by Price have been disclosed.

Methods have e.g. been developed for cold premixing and instantaneous freezing of non-compatible materials in one single container (U.S. Pat. No. 4,295,280), freezing of non-compatible materials at different sites in one container followed by freeze-drying (U.S. Pat. No. 4,351,158) or co-spraying from different nozzles of non-compatible materials into single small droplets, followed by instantaneous freeze-drying (U.S. Pat. No. 4,712,310) in one single container.

Biologically active materials in lyospheres such as enzymes, antibiotics or hormones are currently known from many patents, e.g. U.S. Pat. No. 3,932,943, EPA 448146 and WO 94/25005.

In the field of vaccine production, freeze-drying is a very frequently used way of conservation. In principle, freeze-drying is also applicable for vaccines comprising more than one immunogenic component. This is e.g. the case in EPA 290197, in which a freeze-dried tetravalent vaccine is disclosed. The procedure followed here is simple: the four vaccine components; live viruses, are first mixed and then freeze-dried.

A serious disadvantage of the currently used freeze-drying techniques in the field of vaccine preparation is the following: freeze-drying is known to be a very complex process with many variables, and thus notoriously difficult to perform in a reproducible manner.

This leads to the following problem: especially (but not only) in the field of veterinary vaccines, usually a large number of doses is freeze-dried in one ampoule. Typically a vaccine ampoule comprises 1000 or 2500 doses, and is registered before the Registration Authorities as such. Before freeze-drying, a rough estimation is made about the titre of the material, but the final titre can only be determined after freeze-drying, since, as mentioned, the titre always decreases rather unpredictably during freeze-drying.

As a consequence, in practice a container originally comprising more than 2500 doses often turns out to comprise only 2400 doses after freeze-drying. In that case, the ampoule can only be marketed as a 1000 doses ampoule, since that is the only other officially registered amount of doses.

As a result, animals vaccinated with this vaccine are in fact over-immunised; an unwanted situation. Also, production costs are increasing drastically.

Deliberate increase of the number of doses before freeze-drying is not an alternative: if some vaccine batch is dried more efficiently, one might end up with too high a number of doses from the beginning.

This problem becomes increasingly difficult to solve in the near future, since currently European Registration Authorities are working towards a registration system that only allows vaccines in which the number of doses is between well-defined upper and lower limits. Given the many variables in both the production and the freeze-drying system, it will on a large-scale production basis then be very difficult to remain between these limits.

Especially when a combination vaccine is required, the problem is even more pronounced. Given the fact that it is already difficult to estimate the dose titre left after freeze-drying a single component vaccine, it is increasingly more difficult to assure a well-defined number of doses for each of the vaccine components in multicomponent vaccines.

Additionally, with combination vaccines there is the following problem: as mentioned, in the classical process of freeze-drying as currently in use with vaccine manufacturers, the various components are mixed prior to freeze-drying. Thus, for the preparation of a full range of single/multicomponent-vaccines against e.g. two diseases, three different products must be kept in stock: product comprising anti-A vaccine, product comprising anti-B vaccine, product comprising anti-A and anti-B vaccine.

In the case of vaccines against three diseases, seven different vaccines/combinations have to be made and stored. For example, Protex®-3 for cats (obtainable from Intervet B. V., Boxmeer, The Netherlands) is a freeze-dried vaccine comprising 3 different live attenuated viruses.

For four diseases, this already mounts to fifteen different vaccines/combinations. For instance Progard®-5 for dogs (obtainable from Intervet B. V., Boxmeer, The Netherlands) is a freeze-dried vaccine comprising 4 different live attenuated viruses.

This means a large storage capacity. There clearly is a need for a way of circumventing this problem.

Another serious problem, always specifically encountered in the field of vaccine production is the space-consuming character of the actual freeze-drying process. It is not possible to concentrate very high doses of vaccine material in a very small volume. Therefore, the vials used in classic freeze-drying, containing multiple vaccine doses always contain a relatively large volume of fluid. Essential for freeze-drying is a large size of the surface of this fluid that is in contact with the vacuum. Therefore, since only the top of the frozen pellet is in contact with the vacuum, vaccines are always dried in relatively large bottles, with a wide bottom. These bottles are typically 5 centimeters high, and additional 2 cm of height is needed for the rubber stoppers that are loosely placed on top during freeze drying.

This of course implicates that the ratio of frozen material to empty space in the freeze-drying apparatus is extremely inefficient. This in turn leads to a very cost-ineffective production process. A solution to this problem is highly desirable.

Moreover, due to the fact that always less than 50% (in most cases; only 25%) of the frozen pellet is in direct contact with the vacuum, freeze-drying is very time-consuming. Vaccine components, during freeze-drying, are kept only just below the freezing-point, because otherwise the evaporation of the fluid would require even more time. A long drying period at a temperature just below zero degrees however leads almost inevitably to a decrease of titre.

The present invention gives a direct solution to the above mentioned problems by providing a vaccine container that contains one or more freeze-dried vaccine components, characterised in that said vaccine components are present in two or more freeze-dried bodies, at least one of said bodies being a lyosphere.

A freeze-dried body is understood to be an entity of freeze-dried material. The classic cake, normally found in vials with a freeze-dried material is understood to be such a body. A lyosphere is also understood to be such a body. In one possible embodiment, the vaccine container according to the invention comprises a classic cake as one body and a lyosphere as the other body.

A vaccine container according to the present invention has the advantage that it offers a way to circumvent the problem of the unpredictable loss of titre after freeze-drying.

This can easily be exemplified as follows: for the preparation of a vaccine container containing e.g. 1000 doses of vaccine component, a classic cake is made, with an estimated titre of 900 doses. In order to finally obtain a vaccine container with 1000 doses, first the titre after freeze-drying is determined. Next to this, lyospheres are produced with e.g. an estimated number of 10 doses after freeze-drying. Of these, the exact titre after freeze-drying is also determined. If the titre of the cake turns out to be 850 doses, and that of the lyospheres is 10 doses, it suffices to add 15 lyospheres to the vial with the freeze-dried cake to arrive exactly at the required titre.

It can also be illustrated by the following example: for the preparation of a container containing e.g. 1000 doses of vaccine component, lyospheres are produced with e.g. an estimated number of 100 doses after freeze-drying. The container contains no cake. If it turns out, that each lyosphere after freeze-drying has retained a titre of only 91 doses, it suffices to simply add, instead of the estimated ten lyospheres, eleven lyospheres to the container.

In another embodiment, lyospheres are made which comprise different amounts of doses. For the preparation of a vaccine container containing 1000 doses, 11 lyospheres each comprising 90 doses after freeze-drying and 1 lyosphere comprising 10 doses are added to the container in order to obtain the desired 1000 doses.

Vaccine components are those components that specifically trigger the immune response against the pathogen or pathogens from which the vaccine components were derived.

Such components may originate from one pathogen e.g. an antigenic lipopolysaccharide and an antigenic protein, or e.g. two different antigenic proteins. They may also comprise antigenic parts of a protein or polysaccharide.

These components are generally referred to as subunit components.

In many cases the vaccine component comprises the whole pathogen. The vaccine component can e.g. be a bacterin, or a live attenuated bacterium or virus.

Preferably, a vaccine component is a live (modified) bacterium or virus. Examples thereof are Salmonella bacteria, Newcastle disease virus, Infectious Bronchitis virus and Pseudorabies virus.

Combination vaccines are vaccines comprising various vaccine components.

Combination vaccines may also comprise antigenic components derived from two or more different pathogens.

More complex combinations are also possible. Thus, vaccines of one of the types described above, as well as mixtures thereof are referred to as combination vaccines.

A container is understood to be any useful package of the lyospheres.

The container may e.g. be a glass vial, generally used for packing and storage of vaccines. Adding a diluent to the glass vial to homogeneously dissolve the lyospheres would suffice to make the vaccine ready for use.

Another possible form of a container is a pre-filled syringe, comprising several lyospheres. This syringe can e.g. be filled with the diluent just prior to use. Directly after the lyospheres are homogeneously dissolved, the vaccine is ready for use.

Still another form of packing lyospheres is packing them in blisters. Blisters are usually plastic sheets, with rows of pits containing the lyospheres and covered with alum foil.

This would make it possible to add, directly from a blister, on site in e.g. a chicken-shed just enough lyospheres to e.g. a bowl of drinking water to ensure successful vaccination. Another possibility is to use a sterile plastic straw to store the appropriate amount of lyospheres. This would avoid the use of expensive and space-consuming glass vials.

It is clear that any device that can be used to contain lyospheres can be used in the invention.

A diluent is a fluid that dissolves the lyospheres. This diluent may just be water, or on the other hand it may be a complex mixture of buffers and adjuvans. This will depend mainly on which additives had been added to the lyospheres prior to lyophilisation.

The classic way of freeze-drying, yielding a cake comprising the vaccine component or components in a vial, is space- and time-consuming, as mentioned above. If the vaccine component or components are freeze-dried in the form of lyospheres, they can be spread during the freeze-drying process over the whole surface of the cold plates in the freeze-drying machine. Also they can be stacked, allowing drying various layers of lyospheres at one cold plate.

Additionally, due to the fact that, contrary to the classic situation, no height-consuming vials are involved in this part of the process, the cold plates can be stacked up to a very high density.

As a result, the capacity of freeze-dryers substantially increases, until the condenser capacity has become the limiting factor.

Otherwise, much smaller freeze-dryers could be used.

Therefore in a preferred embodiment, all the freeze-dried bodies in the container are lyospheres.

If a combination vaccine is required, the advantage of the present invention is even more pronounced. It suffices to simply add sufficient lyospheres of each type to the container to end up with a combination vaccine with each component in a perfect dose.

In principle, it is also possible, that the cake and/or some of the lyospheres in the container comprise two vaccine components, and that these are complemented, to the extend needed, with lyospheres comprising a certain amount of one single vaccine component.

At the same time, the present invention offers a solution to the problem of the large storage capacity needed to store all possible variants of e.g. a three- or four-component vaccine.

Instead of mixing the various components prior to freeze-drying as is currently required for the freeze-drying of combination vaccines, each component is freeze-dried separately. Thus the various components can be stored separately. When necessary, each desired combination can instantaneously be made by putting the appropriate amount of lyospheres of each desired component into one container.

This allows for e.g. 4-component combi-vaccines keeping in stock only 4 boxes each comprising lyospheres of one specific type and composing any single or combination vaccine container when it is required, instead of keeping in stock 15 different containers, each comprising a prefabricated component or mixture.

Another very important advantage of the present invention is exemplified as follows: currently, combination vaccines comprising two or more serotypes of one pathogen are made by premixing and freeze-drying the various serotypes of the pathogen. The Registration Authorities require that the titre of each of the different serotypes of the freeze-dried final product is determined separately. This however is in most cases an almost impossible task, due to the fact that antiserum against one serotype almost always cross-reacts with the other serotype(s). Moreover, even when the vaccine components are not serologically related, a non-specific interaction between serum against one component and a non-related other vaccine component in practice often disturbs a correct determination of the titres.

The present invention clearly solves this problem: in order to determine the various titres of the various vaccine components in the lyospheres it suffices to pick from a container one lyospheres of each different serotypes, and to determine the titre of each different lyosphere.

In a preferred form, the vaccine container comprises lyospheres, at least some of which comprise one single vaccine component. These single component lyospheres can then be used to adjust the total amount of each vaccine component in the container.

In a more preferred form, each lyosphere comprises one single vaccine component. Until now, a full range of e.g. fifteen different vaccines based on four vaccine components could only be made by actually preparing fifteen different singles/mixtures, freeze-drying each single/mix in a separate container and stocking each of the fifteen containers. The vaccine container according to the present invention therefore has the following additional advantage: if for example a full range of single/combination vaccines against four different pathogens must be available, it suffices to have four stocks of lyospheres, each with a different vaccine component. By simply adding one or more of the four different lyospheres to a container, each of the fifteen different vaccines and combinations can easily be composed.

In an even more preferred form, the vaccine container comprises vaccine components derived from two or more pathogens. A vaccine based on components from multiple pathogens has the advantage that the single administration of such a vaccine suffices to induce protection against multiple diseases. It is clear, that of each pathogen several different vaccine components may be included.

The size of the various lyospheres is not critical. It is however advantageous if such a size is chosen that the lyospheres can be easily manipulated. For instance, if a well-defined amount of vaccine material of one specific component is included in lyospheres with a well-defined and sufficiently large size that makes them easy to manipulate, then adding just the appropriate amount of these lyospheres to a container suffices to ensure the correct dose of this specific component in the container.

This simplifies the production of vaccines since it avoids difficult quantification steps such as weighing during production. Vaccines based on relatively large lyospheres can be easily composed by simply counting the number of necessary lyospheres for each component.

Therefore, in a preferred embodiment of the invention, the lyospheres have a diameter ranging between 1 and 10 mm.

In another preferred embodiment, the vaccine container according to the present invention comprises coloured lyospheres such that each lyosphere has a colour that is indicative for the contents of said lyosphere. Usually, the vaccine manufacturer marks his various vaccines by capping the containers with multicoloured caps.

The advantage of colouring the various lyospheres is, that it can be checked at first glance and unequivocally which vaccine components are present in the container, and in which dose they are present. This provides a quick, simple and safe double check of the contents of the container.

Usually, the vaccine container will contain between 1 and 10,000 doses of vaccine. Single dose containers are common for individual vaccination, both for human and veterinary use, e.g. for use in cats or dogs.

Human Poliovirus vaccine, human live freeze-dried Typhoid vaccine or Canine Parvovirus vaccine will usually be sold as single dose vaccines. It is obvious, that for the fine-tuning of one single dose of vaccine, the same principle as described for multidose-dose vaccines fully applies.

For the vaccination of large sheds of newly hatched chickens, on the other hand, it is common practice to use a 10,000 doses vaccine container for mass vaccination against Infectious Bronchitis virus.

For the vaccination of large farm-animals such as cattle, against e.g. Infectious Bovine Rhinotracheitis or Parainfluenza virus, vaccine containers with 10 doses are quite commonly in use.

In vaccine containers comprising no classic cake, the number of lyospheres in the vaccine container usually ranges from 2 to 40. Two lyospheres is the minimal amount, to obtain the advantages of the present invention. The number of 40 lyospheres will for practical reasons usually not be exceeded, unless lyospheres with a very small volume are used. If lyospheres with a volume of 100 $\mu$l are used, about 40 lyospheres would fill the average container. Typically, the number of lyospheres in one container will range between 5 and 10.

Usually, the lyospheres, like classical cakes, comprise some stabilisers, e.g. sugars, proteins, fillers such as cellulose, and e.g. agar forming a matrix in order to avoid shrinking during freeze-drying. This matrix also prevents the lyospheres from pulverising after drying. The matrix is understood to be the material that allows the shape of the lyosphere to remain for the most part unaltered during and after freeze-drying. Due to the use of airy matrix material, such as e.g. manitol, or diluted gelatin, agar or agarose solutions, a very airy lyosphere with an unaltered three-dimensional form remains after drying.

One of the advantages of such an airy structure is that it easily redissolves in water. This quickens the administration procedure.

As a result, the matrix material usually applied in classic cakes and lyospheres is very fragile.

Therefore, parenteral applications of classic lyospheres in their nascent form, i.e. in their matrix form is not possible.

Parenteral administration of vaccines embedded in a rigid matrix, the so-called (micro)encapsulation is becoming more and more important.

One of the reasons therefore is, that encapsulated material can be directly implanted in or below the skin, without the use of diluents to homogenise the material.

Implants have been described e.g. by Wise et al. (Adv. Drug Deliv. Rev. 1: 19–39 (1987)). Another advantageous application of encapsulated material is that this encapsulated material is very suitable for oral immunisation. This was e.g. shown by Mestecky et al (J. Controlled Release, 28: 131–141 (1994)), and by Eldridge et al. (Adv. Exp. Med. Biol. 251: 192–202 (1989).

Therefore in a preferred embodiment, the lyospheres in the vaccine container comprise a matrix material that is sufficiently rigid to allow direct transfer of the lyospheres into the recipient, without the need of adding a diluent first.

A rigid matrix is a matrix that prevents the lyosphere from instantaneous collapsing when it is manipulated or comes into contact with a fluid.

A lyosphere with a rigid matrix can easily be obtained by allowing a freeze-dried lyosphere to absorb moist from the air leading to shrinking, followed by another round of freeze-drying during which the lyosphere is fixed in its rigid state.

Such a lyosphere is sufficiently rigid to be implanted in a host.

Another way of obtaining a sufficiently rigid lyosphere is to add a polymer to the starting material from which the lyospheres are made.

Still another way is first producing lyospheres and then surrounding them with a rigid outer shell.

The matrix has to be sufficiently rigid to survive the desired method of administration, e.g. injection or oral application.

The matrix may or may not remain rigid after it is administered to the animal: an implant of a inert, non-degradable material may be envisaged, that slowly releases the vaccine components to the host, and that may if desired, be removed from the host after some time.

On the other hand, a body may be envisaged that is implanted or administered orally, and after hours to weeks, is degraded by the host.

A variety of inert and biodegradable polymers have been described, in Morris et al. (Vaccine 12: 4–11 (1994)), Langer, R. and Moses, M. (J. Cell. Biochem. 45: 340–345 (1991)), in Langer, R. (Meth. Enzymology: 73, 57–74 (1981)).and in Langer, R. (Science 249: 1527–1533 (1990))

The use of these polymers has also been reviewed by Eldridge et al. (Seminars in Haematology 4: 16–25 (1993)).

Most studied polymers for the controlled release of pharmaceuticals are made from lactic and glycolic acids, normal intermediates in mammalian energy metabolism.

If the pore size of the polymer is sufficiently small, compared to the size of the molecules of the embedded vaccine component, the vaccine component or components can only diffuse slowly from the inside of the body into the environment. They are thus only slowly released.

A lyosphere comprising such a polymer thus allows the so-called slow release of the vaccine component. This has the advantage, that the immune system of the recipient is continuously stimulated by the vaccine component over a period of several days to weeks. Such a sustained release has the advantage that it gives a better and more prolonged immunity.

Slow release, also referred to as sustained release, has been reviewed e.g. by Langer, R and Folkman, J. (Nature 263: 797–800 (1976)) and by Preis, I. and Langer, R. S. (Meth. in Enzymology 73: 57–75 (1981)).

Therefore, in a more preferred embodiment of the vaccine container, some of the bodies in the container comprise a matrix that allows slow release of the vaccine component.

The present invention also provides methods for the preparation of a vaccine container according to the present invention, said method being characterised in that it comprises adding one or more lyospheres comprising at least one vaccine component to a container that comprises another freeze-dried body comprising at least one vaccine component.

In an easy form, the method comprises the addition of a lyosphere with a vaccine component to a container that comprises a freeze-dried body in the form of a cake.

Also, a method is provided in which two or more lyospheres comprising at least one vaccine component are added to a container. These lyospheres may comprise the same vaccine component, whereby the amount of vaccine component may or may not differ between the various lyospheres.

In a preferred form, lyospheres are added of which the vaccine components were derived from two or more pathogens.

In a preferred embodiment, lyospheres are added that have a size ranging between 1–10 mm. This has the advantage that they can be easily added by a simple device that is capable of counting these lyospheres, instead of e.g. weighing them, and adding up lyospheres until the correct number is obtained.

Such lyospheres can easily be made by freezing droplets of e.g. 100 $\mu$l. These droplets have a diameter of between 5 and 6 mm after freeze-drying.

In another embodiment, a dye is added to each lyosphere, such that each lyosphere with a specific vaccine component is stained in a specific colour. For this purpose, any dye that is pharmaceutically acceptable can be used.

In still another embodiment, at least one lyosphere is added that comprises a rigid matrix.

In a more preferred form, the matrix of at least one of said added lyospheres is sufficiently dense to allow slow release of the vaccine component.

Finally, the present invention provides a vaccine pack, comprising a vaccine container as described above.

A vaccine pack is understood to be any possible presentation of a vaccine. In a simple form, the vaccine container comprises a vaccine container comprising the vaccine components, packed together with instructions in a box. In a more complex form, that vaccine container could e.g. additionally comprise a diluent and a syringe.

EXAMPLE 1

Preparation of Lyospheres Comprising Live Newcastle Disease Clone 30

Eggs were infected with Newcastle disease virus strain Clone 30 and incubated according to standard methods for growing viruses on eggs.

Allantoïc fluid was harvested.

To 1000 ml of allantoïc fluid, the following materials were added:

66.7 g low fat milk powder

16% stabiliser

The resulting fluid will be called vaccine-fluid. Stabiliser consists of

Tryptose 210 g in

Aqua-dest 1200 ml

Droplets comprising 100 µl of the above mentioned vaccine fluid were quickly cooled to −196° C.

Standard vials (10 ml volume) were filled with 8 frozen droplets each, and the vials were placed in a freeze-dryer.

Good care was taken to keep the lyospheres frozen during all manipulations.

Freeze-drying was done fully according to standard procedures.

Comparison of Lyosphere-Titre and Cake-Titre

In this test, two groups of vials were used: standard vials (10 ml volume) were filled with 8 lyospheres each as described above, and comparable vials, filled with 2 ml of the above mentioned vaccine fluid were freeze-dried. These two groups of vials; vials with lyospheres and vials with classic freeze-dried cake were used in titre-comparison experiments.

Two experiments were done; one with live attenuated Infectious Bronchitis virus IB H120 batch 05098A and one with live attenuated Newcastle disease virus LaSota batch 05088B.

A correction was made for the fact, that the volume used for the preparation of the vials with the cakes is 2 ml, whereas the vials with lyospheres comprise only the equivalent of 0.8 ml.

TABLE 1A

Titres IB H120 batch 05098A

|  | titre after freeze-drying |
|---|---|
| vials | 8.4 |
| lyospheres | 8.3 |

TABLE 1B

Titres ND LaSota batch 05088B

|  | titre after freeze-drying |
|---|---|
| vials | 10.1 |
| lyospheres | 10.2 |

As is clear from table 1A and 1B, the titres of both the cakes and the lyospheres are fully comparable.

It must be mentioned here, that the lyospheres were dried in vials, together with the vials containing the classic cakes. Drying time was as usual for vials with classic cakes.

Therefore, this experiment does not show any stabilising effects of shorter drying times for lyospheres.

Comparison of Necessary Freeze-Drying Volume of Lyospheres Compared to Classic Vials Current method; vials with cakes:

The diameter of the vials is 22 mm. At each $m^2$ of surface in the freeze-drying-apparatus 2340 vials can be placed. Given the total surface capacity of the freeze-drying apparatus, the volume to be dried in one run is 20.2 liters, see table 2.

Lyosphere method:

The diameter of the spheres is 5.75 mm for the 100 µl lyospheres, and 4.57 mm for the 50 µl lyospheres. They can be stacked at least in 3 layers. The number of lyospheres at each $m^2$ is 34600 or 54936 respectively per layer. All experiments have been done with three layers. Given the total surface capacity of the freeze-drying apparatus, the volume to be dried in one run is 89.4 liters, see table 2.

The capacity of the condenser (100 kg ice) of the freeze-drying apparatus is the limiting factor in these experiments.

TABLE 2

|  | diam. | Max. # liters vaccine |
|---|---|---|
| current 1 ml/vial | 22 mm. | 20.2 litre |
| lyospheres 100 µl | 5.75 mm. | 89.4 litre |
| lyospheres 50 µl | 4.57 mm. | 71.1 litre |

Table 2 shows, that if the vaccine fluid is freeze-dried in the form of 100 µl lyospheres, a total volume of 89.4 liters of vaccine fluid can be dried in one run, whereas if the classical method is used, 20.2 liters can be dried in one run. Therefore, drying 100 µl lyospheres increases the efficiency about 4.4 times over the classic approach.

We claim:

1. A vaccine container that contains one or more freeze-dried vaccine components, wherein said vaccine component or components are present in two or more freeze-dried bodies, wherein at least one body has only a single vaccine component and at least one of said bodies being a lyosphere.

2. The vaccine container according to claim 1, wherein the freeze-dried bodies are lyospheres.

3. The vaccine container according to claim 1, wherein each body comprises one single vaccine component.

4. The vaccine container according to claim 1, wherein the vaccine components are derived from two or more pathogens.

5. The vaccine container according to claim 1, wherein the lyospheres have a diameter ranging between 1 and 10 mm.

6. The vaccine container according to claim 1, wherein each body has a color that is indicative for the contents of said lyosphere.

7. The vaccine container according to claim 1, wherein at least one of the bodies comprises a rigid matrix.

8. The vaccine container according to claim 7, wherein the matrix allows slow release of the vaccine component.

9. A method for the preparation of a vaccine container according to claim 1, comprising adding one or more lyospheres comprising at least one vaccine component to a container that comprises another body comprising at least one vaccine component.

10. A method for the preparation of a vaccine container according to claim 2, wherein it comprises adding two or more lyospheres comprising at least one vaccine component to a container.

11. A vaccine pack, comprising a vaccine container according to claim 1.

12. A vaccine container that contains one or more freeze-dried vaccine components, wherein said vaccine component or components are present in two or more freeze-dried bodies, at least one of said bodies being a lyosphere and having a diameter ranging between 1 and 10 mm.

* * * * *